(12) United States Patent
Cohen et al.

(10) Patent No.: US 11,696,987 B2
(45) Date of Patent: Jul. 11, 2023

(54) DRUG INJECTION DEVICE

(71) Applicant: Stevanato Group S.P.A., Piombino Dese (IT)

(72) Inventors: Philip Jake Cohen, London (GB); Frances Anne Penrose, Ely (GB); Conor Devine, Cambridge (GB)

(73) Assignee: Stevanato Group S.P.A., Piombino Dese (IT)

( * ) Notice: Subject to any disclaimer, the term of this patent is extended or adjusted under 35 U.S.C. 154(b) by 0 days.

(21) Appl. No.: 17/662,854

(22) Filed: May 11, 2022

(65) Prior Publication Data

US 2022/0362477 A1 Nov. 17, 2022

(30) Foreign Application Priority Data

May 11, 2021 (IT) .................... 102021000012020

(51) Int. Cl.
*A61M 5/315* (2006.01)

(52) U.S. Cl.
CPC .... *A61M 5/31541* (2013.01); *A61M 5/31553* (2013.01)

(58) Field of Classification Search
CPC .......... A61M 5/31541; A61M 5/31533; A61M 2005/3154

See application file for complete search history.

(56) References Cited

U.S. PATENT DOCUMENTS

| 10,569,024 | B2 | 2/2020 | Harms et al. | |
|---|---|---|---|---|
| 2009/0043264 | A1* | 2/2009 | Glejbol | A61M 5/31551 604/211 |
| 2012/0283648 | A1 | 11/2012 | Veasey et al. | |
| 2013/0178803 | A1* | 7/2013 | Raab | A61M 5/31585 604/211 |
| 2016/0045673 | A1* | 2/2016 | Bayer | A61M 5/31583 604/209 |
| 2016/0220759 | A1* | 8/2016 | Enggaard | A61M 5/3158 |
| 2019/0366007 | A1* | 12/2019 | Hewson | A61M 5/31536 |

FOREIGN PATENT DOCUMENTS

| WO | WO-9626754 A2 * | 9/1996 | ........ A61M 5/31551 |
|---|---|---|---|
| WO | WO-2020205255 A1 * | 10/2020 | ........ A61M 5/31541 |

* cited by examiner

*Primary Examiner* — Dung T Ulsh
(74) *Attorney, Agent, or Firm* — Husch Blackwell LLP

(57) ABSTRACT

A drug injection device includes a housing with a cartridge having a predetermined drug volume, a dose setting mechanism for setting a drug dose, and a dose delivery mechanism. A dose setting service element rotates about a longitudinal axis during the drug dose setting. The dose setting mechanism has a last dose setting device to prevent setting of a drug dose greater than the drug volume remaining in the cartridge. The last dose setting device includes a pinion coaxial with the longitudinal axis that rotates about the longitudinal axis with the dose setting service element during drug dose setting, and a rack engaged with the pinion that moves parallel to the longitudinal axis when the pinion rotates. The pinion and the rack have mutual abutment elements that prevent further rotation of the pinion after the rack has travelled an axial length correlated to the predetermined drug volume.

14 Claims, 7 Drawing Sheets

DRUG INJECTION DEVICE

CROSS REFERENCES

This application claims priority to Italian Application No. 102021000012020 filed on May 11, 2021, the disclosure of which is expressly incorporated by reference herein in its entirety.

TECHNICAL FIELD

The present invention relates to a drug injection device. More particularly, the invention relates to a drug injection device of the type allowing a user to set a desired dose of a predetermined drug volume contained in a cartridge and to deliver the previously set desired dose to a injection site, the set and delivery operation being repeatable till the whole drug volume contained in the cartridge is delivered.

BACKGROUND

Examples of drug injection devices of the type discussed above are described in DE 202012001411U1 and U.S. Pat. No. 8,512,296B2. These devices are appreciated by the users as being compact and user-friendly.

U.S. Pat. No. 10,569,024B2 and US 2019/0366007A1 disclose drug injection devices which, in addition to comprising members configured to allow the user to set a desired dose before delivering such a dose, further comprise members configured to prevent the user to set a dose exceeding the dose volume remaining in the cartridge after having delivered one or more doses. In particular, in U.S. Pat. No. 10,569,024B2 such an exceeding dose is prevented to be set by an abutment between a stop member fixed to a piston rod and a stop member fixed to a nut member configured to move along the piston rod, whereas in US 2019/0366007A1 the abovementioned exceeding dose is prevented to be set by an abutment between a nut configured to move along a drive shaft and a worm gear fixed to an end of the drive shaft.

The Applicant has considered the benefit of preventing the user to be able to set a dose greater than the one currently available in the cartridge.

Accordingly, the Applicant has designed a drug injection device wherein this benefit is achieved by a technical solution different from those of the prior art.

SUMMARY OF THE DISCLOSURE

Therefore, the present invention relates to a drug injection device that includes:
- a cartridge housing extending along a longitudinal axis and configured to house a cartridge including a predetermined drug volume;
- a dose setting mechanism configured to set a drug dose to be delivered out of the cartridge;
- a dose delivery mechanism configured to deliver the drug dose set by the dose setting mechanism;
- wherein the dose setting mechanism comprises:
- a dose setting service element configured to rotate about said longitudinal axis during the drug dose setting;
- a last dose setting device configured to prevent a user to set a drug dose greater than the drug volume remaining in the cartridge after at least one previous drug dose delivery, wherein the last dose setting device comprises:
- a pinion arranged coaxially to said longitudinal axis at a fixed axial position with respect to the cartridge housing and configured to rotate about the longitudinal axis together with the dose setting service element during the drug dose setting;
- a rack engaged with the pinion and movable along a longitudinal direction parallel to the longitudinal axis when the pinion rotates;
- wherein the pinion and the rack have mutual abutment elements configured to abut with each other and prevent further rotation of the pinion after the rack has travelled an axial length correlated to the predetermined drug volume.

Throughout the present description and in the annexed claims, the term "axial" and the corresponding term "axially" are used to refer to a longitudinal direction of the injection device, which corresponds to the longitudinal direction of the cartridge housing, whereas the term "radial" and the corresponding term "radially" are used to refer to a any direction perpendicular to the abovementioned longitudinal direction. In particular, when referring to components which rotate about an axis, the terms "radial" and radially" are used to indicate any direction perpendicular to such an axis.

A longitudinal direction oriented from the hand of the user who handles the injection device during the injection operation toward the injection site (for example the skin of a patient) is herein also referred to with the term "distal direction", whereas a longitudinal direction oriented from the injection site toward the hand of the user who handles the injection device during the injection operation is herein also referred to with the term "proximal direction".

The term "correlated" is used to indicate a mutual dependency relationship between two parameters, like for example two linear dimensions or a linear dimension and a volume. This means that the amount or size or extent of a first parameter is a function of (or depends on) the amount or size or extent of a second parameter and/or vice versa.

The Applicant has perceived that the provision in the drug injection device of a pinion-rack coupling wherein, during each dose setting operation, the pinion is prevented to move axially with respect to the dose setting service element while being driven in rotation by the dose setting service element and the rack moves with respect to the cartridge housing due to the engagement with the pinion causes, during the first dose setting operation and any further dose setting operation subsequent to the first dose delivery operation, for the rack to travel a corresponding partial axial length which depends on the specific dose actually set and delivered each time, so that from the first dose setting and delivery operation to the last dose setting and delivery operation the rack travels a total axial length which depends on the maximum dispensable drug volume provided within the cartridge.

Consequently, the Applicant has though that the provision in the pinion and in the rack of respective abutment elements configured to abut with each other when the rack has travelled the abovementioned total axial length obstruct a further rotation of the pinion (and therefore of the dose setting service element) after having reached, during any further dose setting operation subsequent to the first dose delivery operation, a dose equal to the dose volume currently present in the cartridge, thus preventing the user to set a dose greater than the one still available.

Preferred features of the drug injection device of the invention are disclosed below, each of these features being provided individually or in combination with the other preferred features.

Preferably, the injection device is of the pen-type, so as to allow an easy portability, handling, storing and operation of the injection device by the user.

The injection device of the invention is compact irrespective of the provision of the last dose setting device. For example, the size of the injection device can be the same as that of the injection devices of DE 202012001411U1 and U.S. Pat. No. 8,512,296B2, which do not include any last dose setting devices.

The injection device can be of the re-usable or disposable type, whereas the disposable use is the most preferred one.

Preferably, during the drug dose setting the dose setting service element does not move along said longitudinal direction.

Preferably, the dose setting service element is configured to move along said longitudinal direction toward the cartridge housing (thus along the distal direction) during the drug dose delivery. Thus, the dose setting mechanism and the dose delivery mechanism share a same structural element (namely, the dose setting service element), to the benefit of the compactness of the injection device.

Preferably, during the drug dose delivery the dose setting service element does not rotate about said longitudinal axis.

The rotational movement of the dose setting service element only during the dose setting operation and the axial movement of the dose setting service element only during the dose delivery operation allow these two operations to be structurally and functionally separate from each other while sharing a same structural element, namely the dose setting service element.

Preferably, the rack has a predetermined axial dimension which is correlated to an axial length travelled by the dose setting service element for delivering the predetermined drug volume.

This specific provision allows to select the specific axial dimension of the rack depending on the specific drug volume contained in the cartridge to be used, thus ensuring an identical effective operation of the injection device when new cartridges having the same volume of drug are used.

Preferably, before setting a first drug dose the pinion is located at a first free end of the rack closer to the cartridge housing.

Preferably, after having set the last drug dose the pinion is located at a second free end of the rack opposite to said first free end of the rack.

In this way the axial length travelled by the rack from the first dose setting and delivery operation to the last dose setting and delivery operation is equal to the axial dimension of the rack.

Preferably, said mutual abutment elements comprise a first rotational end stop element associated with the pinion.

Preferably, said mutual abutment elements comprise a second rotational end stop element associated with the rack.

The term "rotational end stop element" is used herein to indicate an element which abuts against another element upon rotation of at least one of the two elements about a respective rotation axis.

In the injection device of the invention, the provision of rotational end stop elements allows an effective stop to the rotation of the pinion and, accordingly, to the axial movement of the rack during the last dose setting operation.

Preferably, the first rotational end stop element is associated with a face of the pinion located on the opposite side with respect to the cartridge housing.

Preferably, the second rotational end stop element is arranged at the second free end of the rack.

Preferably, the rack is slidingly coupled to an outer case of the drug injection device.

Preferably, the rack comprises an axial guide groove slidably coupled to an axial guide rail provided on an internal surface of the outer case of the drug injection device. This axial coupling allows an easy and precise mounting of the rack within the outer case as well as a self-centering feature that further promotes the axial movement of the rack with respect to the outer case.

Preferably, the pinion is arranged between the rack and at least one rib formed on the internal surface of the outer case on the opposite side with respect to the rack. Such a rib acts as a limiter for the radial movement of the pinion to avoid a disengagement of the pinion from the rack in case of shocks.

Preferably, two ribs are provided on the internal surface of the outer case on opposite sides with respect to a radial plane of the pinion coinciding with a longitudinal median plane of the rack. This provision allows a more effective contrast against any possible disengagement movement of the pinion with respect to the rack.

Preferably, the dose setting service element has at least one planar surface and the pinion has at least one planar profile portion coupled to the at least one planar surface of the dose setting service element. This allows an effective rotational coupling between pinion and dose setting service element during the dose setting operation as well as an effective sliding coupling between pinion and dose setting service element during the dose delivery operation.

In preferred embodiments, the dose setting service element is a piston rod extending along said longitudinal axis.

In these embodiments, preferably, the pinion has a central hole coupled with the piston rod and said at least one planar profile is defined by a surface portion of said central hole.

BRIEF DESCRIPTION OF THE DRAWINGS

Further features and advantages of the present invention will become clearer from the following detailed description of preferred embodiments thereof, made with reference to the attached drawings and given for indicating and not limiting purposes. In such drawings.

DETAILED DESCRIPTION

Figure 1:
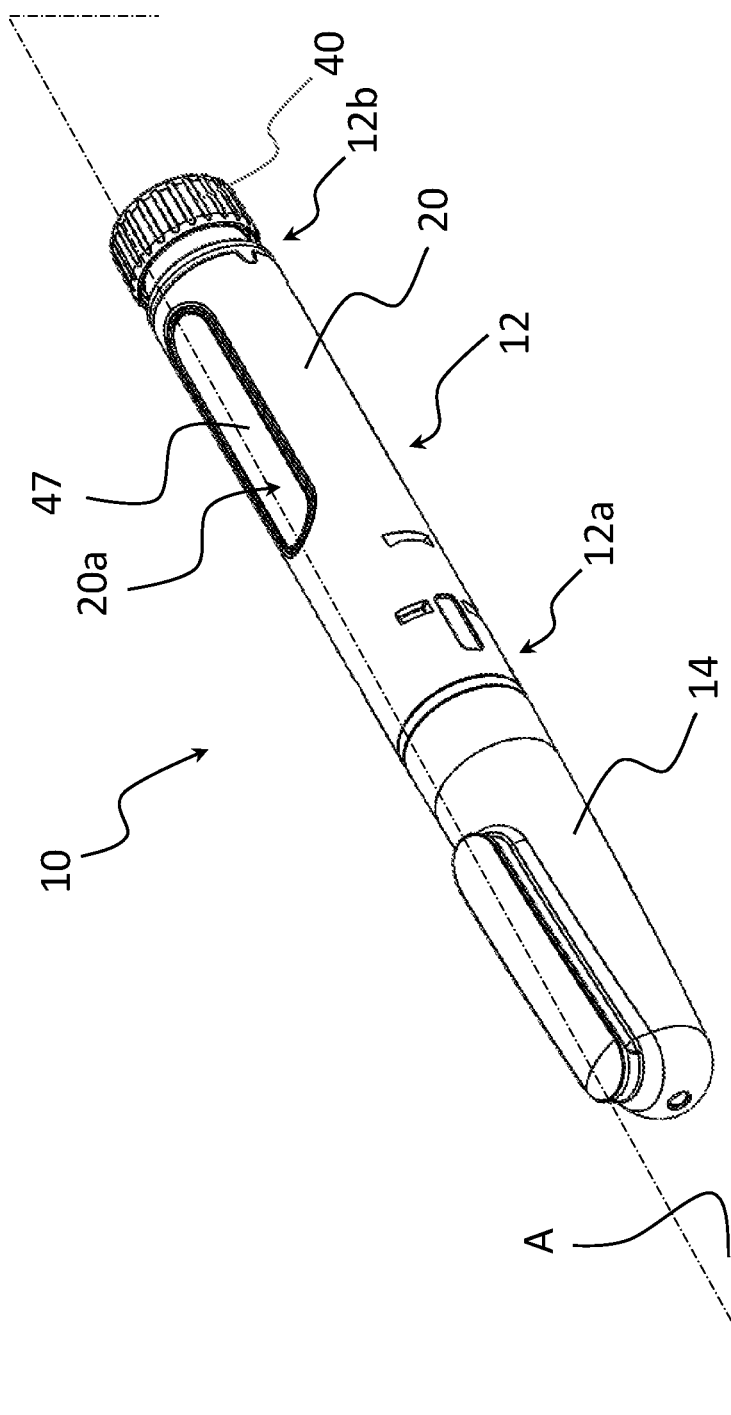
FIG. 1 is a schematic perspective view of an embodiment of a drug injection device according to the present invention.
Figure 2:
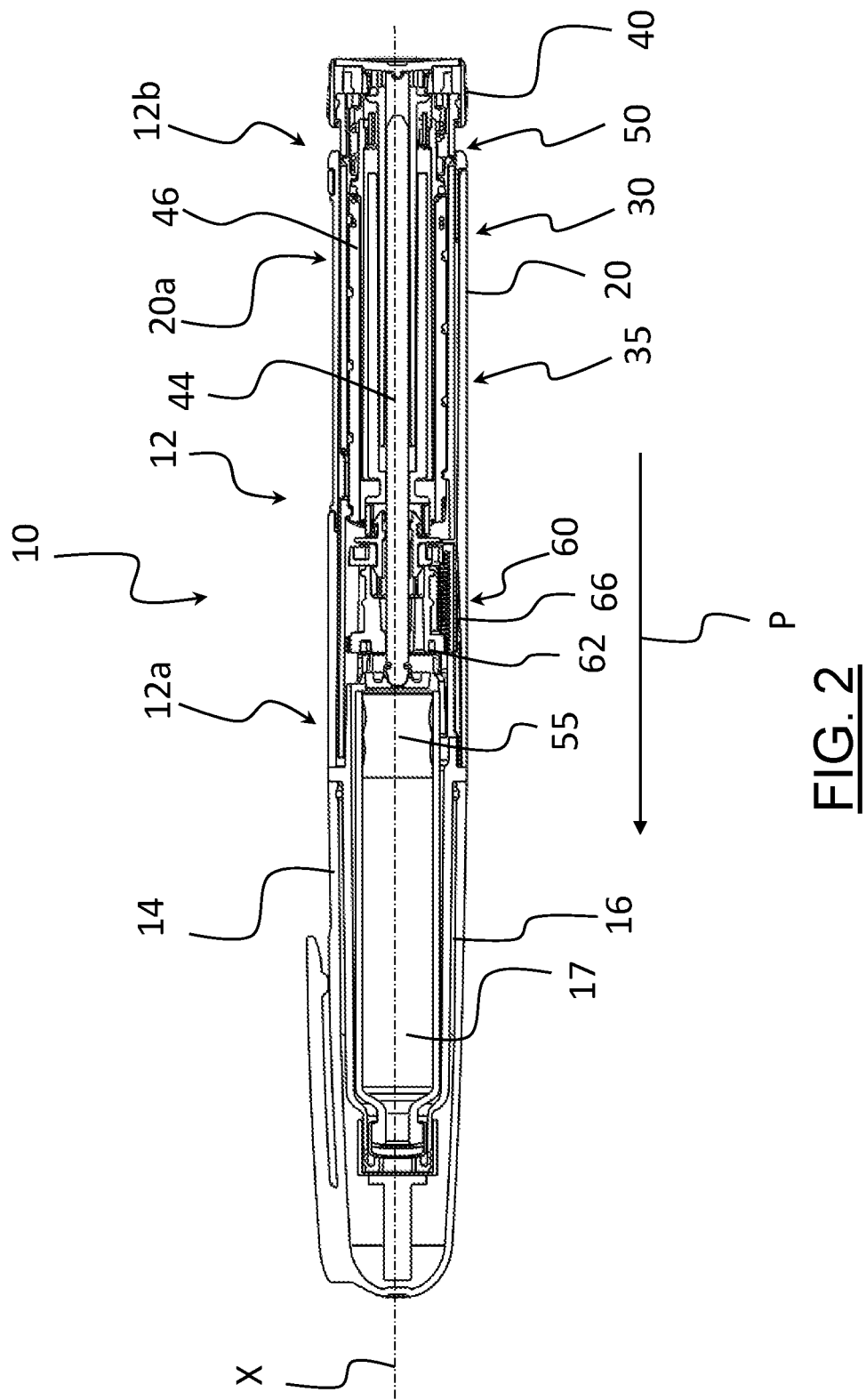
FIG. 2 is a schematic sectional view of the injection device of FIG. 1 taken at the sectional plane labelled with A in FIG. 1.

An embodiment of a drug injection device 10 according to the present invention is shown in FIGS. 1 and 2.

The injection device 10 is of the pen-type and extends along a central longitudinal axis X, shown in FIG. 2.

The injection device 10 includes a main body 12 and a cap case 14 removably associated with the main body 12 at a first free end 12a of the main body 12.

Both the main body 12 and the cap case 14 when the latter is coupled to the main body 12, extend coaxially to the longitudinal axis X.

A cartridge housing 16 extending coaxially with the longitudinal axis X is removably coupled to the main body 12 at the first free end 12a so as to be housed within the cap case 14 when the latter is coupled to the main body 12. The cartridge housing 16 is configured to house a cartridge 17 including a predetermined drug volume to be delivered.

The main body 12 comprises an outer case 20, which preferably is substantially cylindrically-shaped.

A dose setting mechanism 30 and a dose delivery mechanism 35 are provided within the outer case 20. The dose setting mechanism 30 is configured to allow a user to set a drug dose to be delivered out of the cartridge 17, whereas the dose delivery mechanism 35 is configured to allow the user to deliver the drug dose set by the dose setting mechanism 30.

As many different kinds of dose setting mechanism 30 and dose delivery mechanism 35 can be foreseen in the injection device 10 of the invention, they are not described in detail herein. For example, the dose setting mechanism 30 and dose delivery mechanism 35 can be of the same type as described in DE 202012001411U1 and U.S. Pat. No. 8,512, 296B2. In this specific case and as it will be clearer from the description below, the dose delivery mechanism 30 of the injection device 10 differs from the one of the devices of these two prior art documents in that it further includes a last dose setting device 60, shown in FIG. 2 and described in more details below with reference to FIGS. 3-6.

The dose setting mechanism 30 and the dose delivery mechanism 35 share a knob 40 provided at a second free end 12b of the main body 12 opposite the first free end 12a thereof and a dose setting service element arranged within the outer case 20 coaxially to the longitudinal axis X and having a free end operatively connected to the knob 40.

In the embodiment herein shown, the abovementioned dose setting service element is a piston rod 44 extending coaxially to the longitudinal axis X.

The knob 40 is configured to be driven by the user in rotation clockwise and counterclockwise about the longitudinal axis X to drive the dose setting mechanism 30 and to be pushed by the user along a longitudinal (or distal) direction P parallel to the longitudinal axis X to drive the dose delivery mechanism 35.

The rotation is herein intended as clockwise or counterclockwise when looking a right side view of the injection device 10 when the latter is positioned as shown in FIG. 2, that is when looking at the knob 40 from a side opposite to the side where the cartridge 17 is provided.

A clutch device 50 is provided within the outer case 20 to switch the injection device 10 between a dose setting configuration wherein the clutch device 50 is operatively connected to the knob 40 and operatively connects the knob 40 to the dose setting mechanism 30, and a dose delivery configuration wherein the clutch device 50 is operatively disconnected from the knob 40 and the latter is operatively connected to the dose delivery mechanism 35.

In the dose setting configuration, the piston rod 44 rotates about the longitudinal axis X and is prevented to move along the longitudinal direction P, whereas in the dose delivery configuration the piston rod 44 moves along the longitudinal direction P and is prevented to rotate about the longitudinal axis X.

The piston rod 44 is coupled to a dose setting sleeve 46 which rotates about the longitudinal axis X both in the dose setting configuration and in the dose delivery configuration. In the dose setting configuration, the rotation of the dose setting sleeve 46 and of the piston rod 44 is driven by the clutch device 50 which in turn is driven by the rotation of the knob 40 about the longitudinal axis X, whereas in the dose delivery configuration the rotation of the dose setting sleeve 46 is caused by an axial thrust exerted by the user on the knob 40 along the longitudinal direction P.

The dose setting sleeve 46 comprises an outer surface 47 (shown in FIG. 1) having a plurality of numbers (or generally indicia, not shown), each number being correlated to a respective dose of all the settable doses.

As shown in FIG. 1, a display window 20a is formed in the outer case 20.

The user rotates the knob 40 clockwise or counterclockwise till the number correlated to the desired dose to be set and delivered is displayed through at the display window 20a, thus providing the user with a visual indication about the dose actually set. Rotation in both directions during the dose setting operation allows the user to set the desired dose in case he/she initially sets a dose greater or lower than the desired dose.

Once the desired dose has been set, the user pushes the knob 40 along the longitudinal direction P to deliver such a dose. The axial movement of the knob 40 causes the clutch device 50 to switch the injection device 10 from the dose setting configuration to the dose delivery configuration. In the latter configuration the knob 40 is prevented to rotate.

A stopper 55 (shown in FIG. 2) is coupled to the free end of the piston rod 44 opposite to the knob 40. The stopper 55 is initially inserted within the cartridge 17, provided within the cartridge housing 16, at a free end of the cartridge 17 located at the free end 12a of the main body 12. Due to the axial movement of the piston rod 44 caused by the axial movement of the knob 40 during the dose delivery operation, the stopper 55 axially moves within the cartridge 17 along the longitudinal direction P toward the opposite free end of the cartridge 17 thus forcing the desired dose to exit from the cartridge 17 at the opposite free end thereof.

A last dose setting device 60 is arranged between the dose setting sleeve 46 and the cartridge housing 16 in order to prevent the user to set a dose greater than the one remaining in the cartridge 17 after the previous dose delivery/ies.

As shown in FIGS. 3-7, the last dose setting device 60 comprises a pinion 62 coupled within the outer case 20 at a fixed axial position of the outer case 20 and a rack 66 engaged with the pinion 62 and slidingly coupled with an internal surface of the outer case 20.

Figure 5:
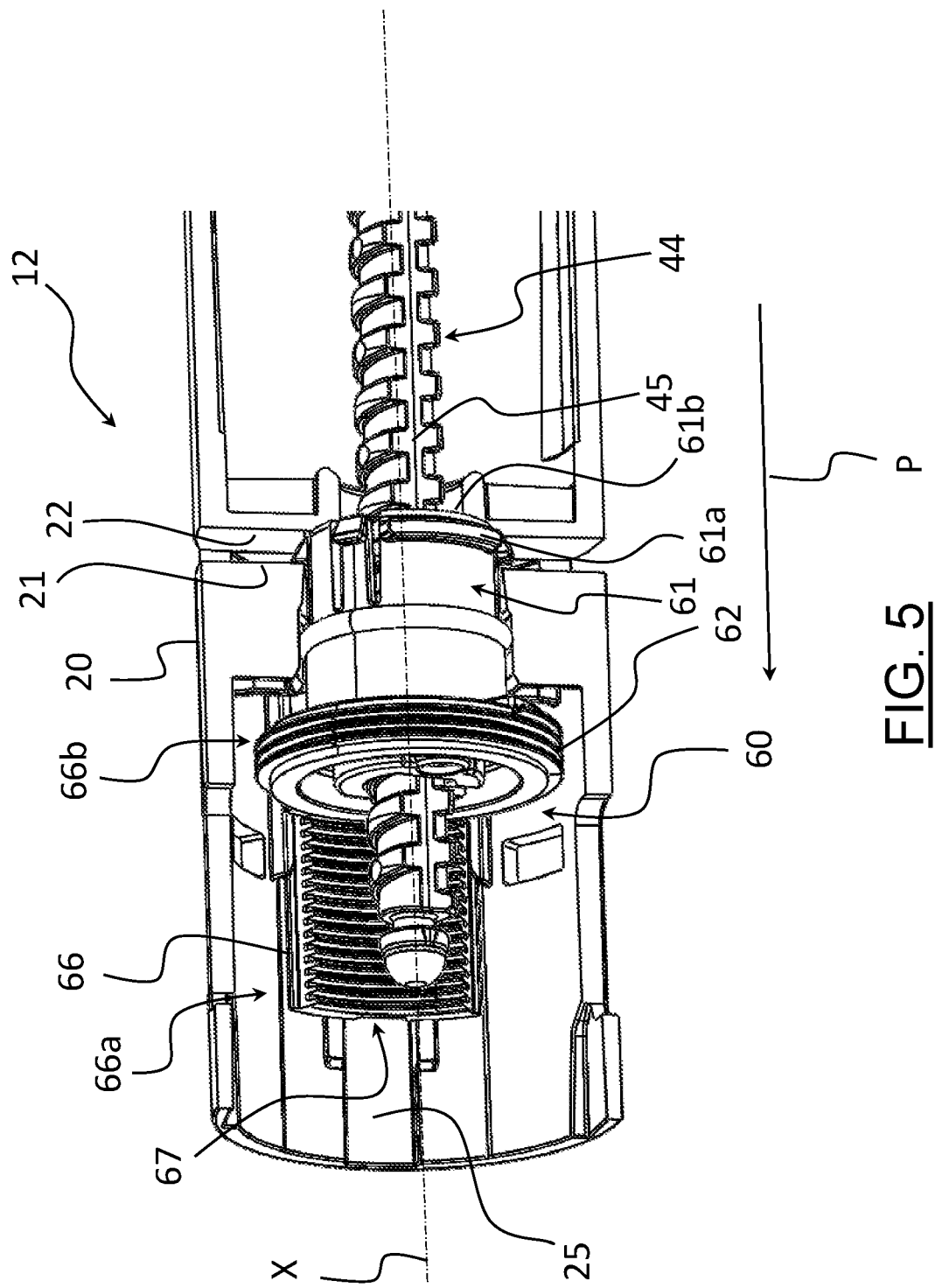

As shown in FIG. 5, the fixed axial position of the pinion 62 within the outer case 20 is defined by positioning a collar 61a formed at a free end of a mandrel 61 of the pinion 62 in abutment against an abutment surface 21 projecting radially inwardly from the internal surface of the outer case 20 and by positioning a free end portion 61b (or the collar 61a) of the mandrel 61 in abutment against another abutment surface 22 projecting radially inwardly from the internal surface of the outer case 20.

The pinion 62 is arranged coaxially to the longitudinal axis X and includes a central hole 64 coupled with the piston rod 44.

The coupling between the pinion 62 and the piston rod 44 is such that during the dose setting operation the piston rod 44 drags in rotation the pinion 62 whereas during the dose delivery operation the piston rod 44 slides axially within the central hole 64.

In order to allow the rotational coupling between the pinion 62 and the piston rod 44, the piston rod 64 has a longitudinal planar surface 45 and the central hole 64 has a planar profile portion 65 coupled to the longitudinal planar surface 45.

In order to prevent the pinion 62 from disengaging from the rack 66 in case of shocks, two ribs 63 (only one of which can be seen in FIG. 3) are formed on the internal surface of the outer case 20 on a portion of the latter arranged on the opposite side of the rack 66, so that the pinion 62 is arranged between the ribs 63 and the rack 66. The ribs 63 are preferably located on the opposite sides with respect to a radial plane of the pinion 62 coinciding with a longitudinal median plane of the rack 66.

Due to the fixed axial position of the pinion 62 within the outer case 20, when the pinion 62 rotates the rack 66 moves along the longitudinal direction P. Preferably, a clockwise rotation of the pinion 62 causes an axial movement of the rack 66 toward the cartridge housing 16, that is along the distal direction, whereas a counterclockwise rotation of the pinion 62 causes an axial movement of the rack 66 toward the dose setting sleeve 46, that is along the proximal direction.

The axial movement of the rack 66 is obtained thanks to the sliding coupling between an axial guide groove 67 formed in the rack 66 and extending along the longitudinal direction X and an axial guide rail 25 provided on an internal surface of the outer case 20 and also extending along the longitudinal direction X.

The rack 66 is designed such that the axial length travelled by the rack 66 during all the dose setting operations performed in order to delivery the maximum dispensable drug volume initially contained in the cartridge 17 is correlated to such a whole drug volume.

Figure 7:
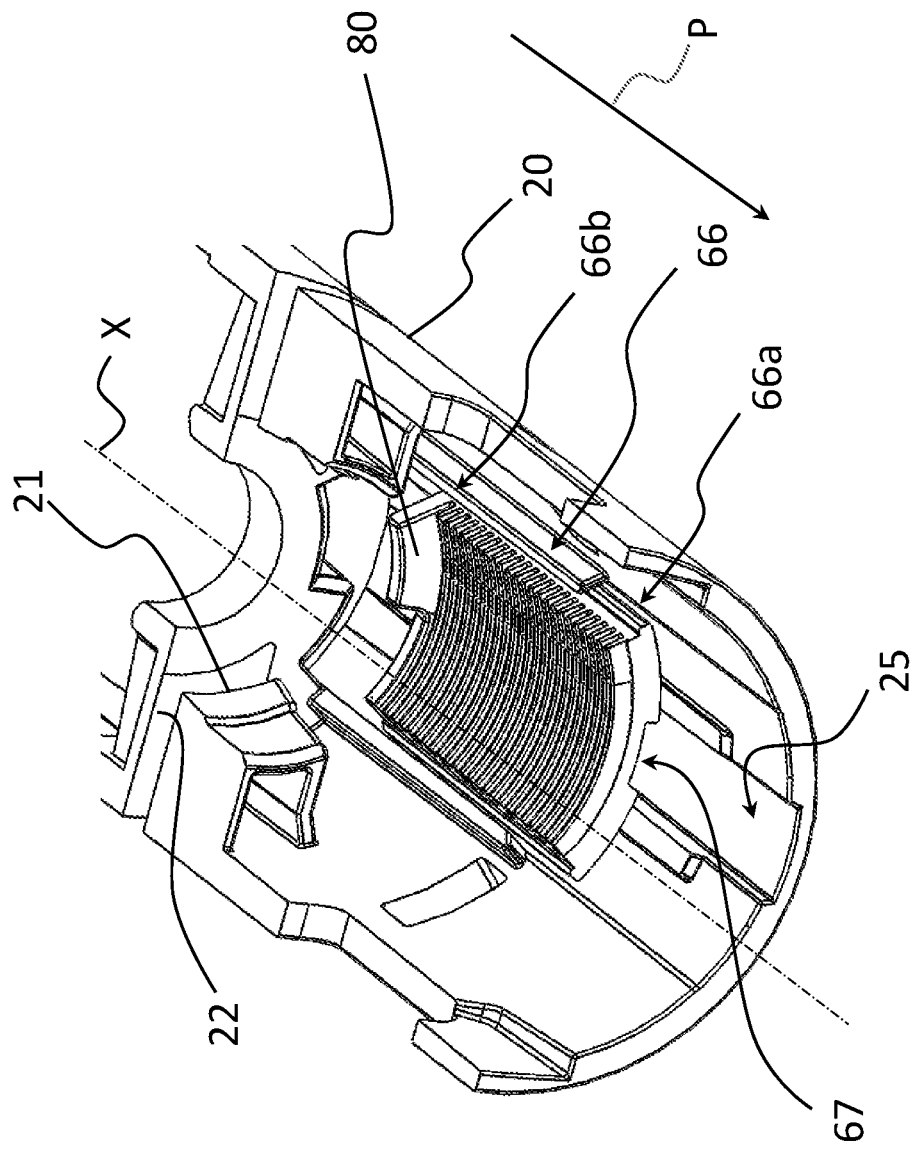
FIG. 7 is a perspective view of a component of the last dose setting device of FIGS. 3-6.

The rack 66 comprises a free end 66a closer to the cartridge 17 and an opposite free end 66b, as shown in FIGS. 5 and 7.

In particular, the rack 66 has a predetermined axial dimension which is equal or proportional to an axial length travelled by the piston rod 44 for delivering the abovementioned whole drug volume.

Figure 6:
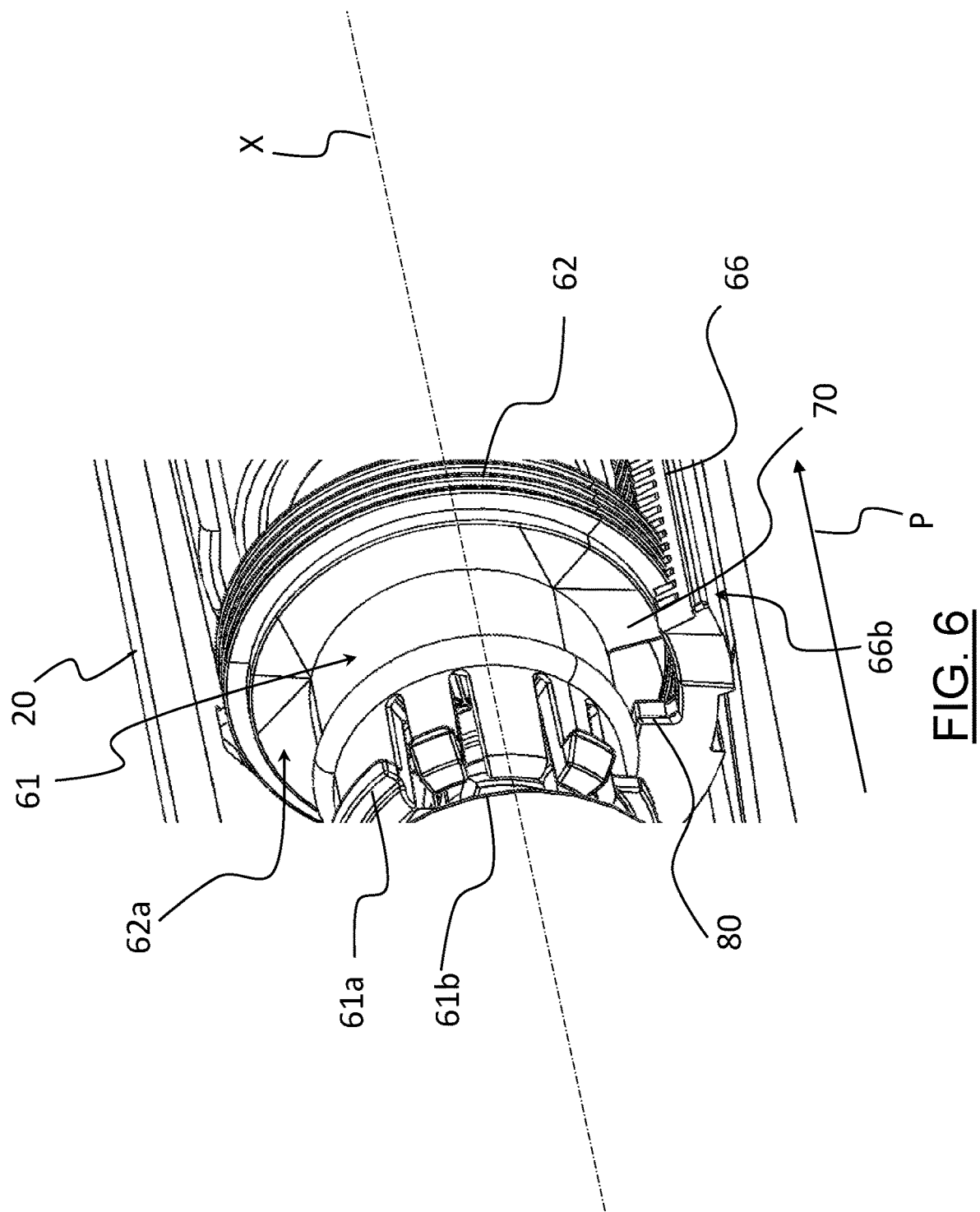
FIG. 6 is a schematic enlarged perspective view of the last dose setting device of FIG. 4 in the same operative configuration of FIG. 5 but from an opposite point of view.

As shown in FIG. 6, a rotational end stop element 70 is provided in a face 62a of the pinion 62 faced toward the second free end 66b of the rack 66 and a corresponding rotational end stop element 80 is provided in the rack 66 at the second free end 66b thereof.

During the rotation of the pinion 62, and consequently during the axial movement of the rack 66, when the rotational end stop element 70 abuts to the rotational end stop element 80 further rotation of the pinion 62, and consequently further axial movement of the rack 66, is prevented.

Figure 3:
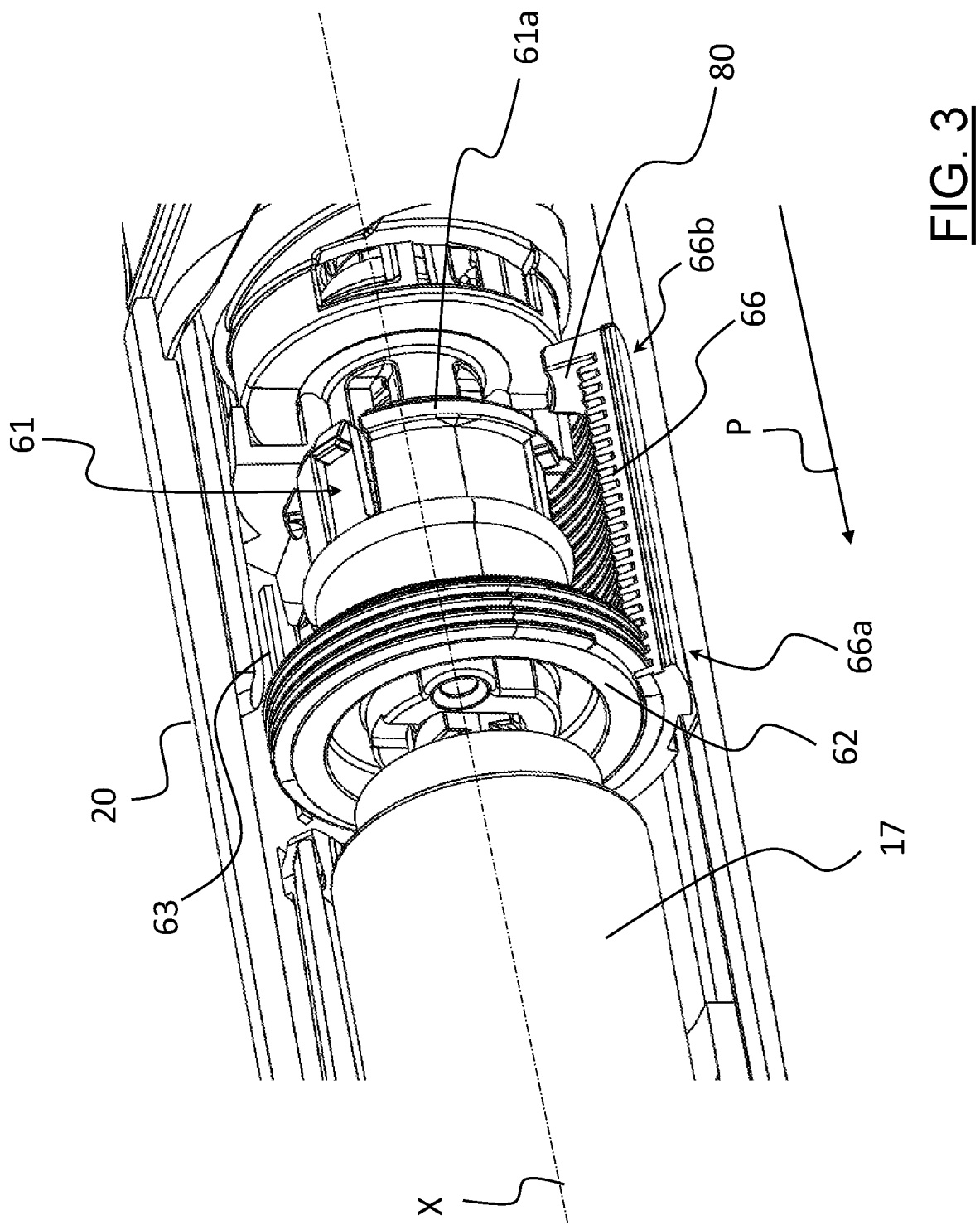
FIG. 3 is a schematic perspective view of a last dose setting device provided within the injection device of FIG. 1 in a first setting configuration thereof.

In operation, the injection device 10 is initially in the dose setting configuration and the user rotates the knob 40 to set the desired dose to be delivered. During such a first dose setting operation the knob 40 moves axially along the proximal direction, while rotating. As shown in FIG. 3, the rack 66 is initially arranged at a first position such that the pinion 62 is located at the free end 66a of the rack 66 and during the first dose setting operation the rack 66 moves from such a first position toward the cartridge 17 along the longitudinal direction P (that is the distal direction) travelling an axial length which depends on the specific dose actually set. Once the first dose setting operation is concluded, the rack 66 is at a second axial position closer to the cartridge 17.

After such a first dose setting operation is concluded, the user pushes the knob 40 toward the cartridge 17 along the longitudinal direction P to deliver the dose previously set. During such a first dose delivery operation the rack 66 does not move from the second axial position previously reached.

After such a first dose delivery operation, when the user wishes to set a new desired dose to be delivered, the user rotates the knob 40 to set such a new desired dose. During such a new dose setting operation the piston rod 44 remains at the axial position reached at the end of the first dose delivery operation till the end of the new dose setting operation, while the rack 66 moves toward the cartridge 17 travelling a respective axial length which depends on the new desired dose actually set.

Figure 4:
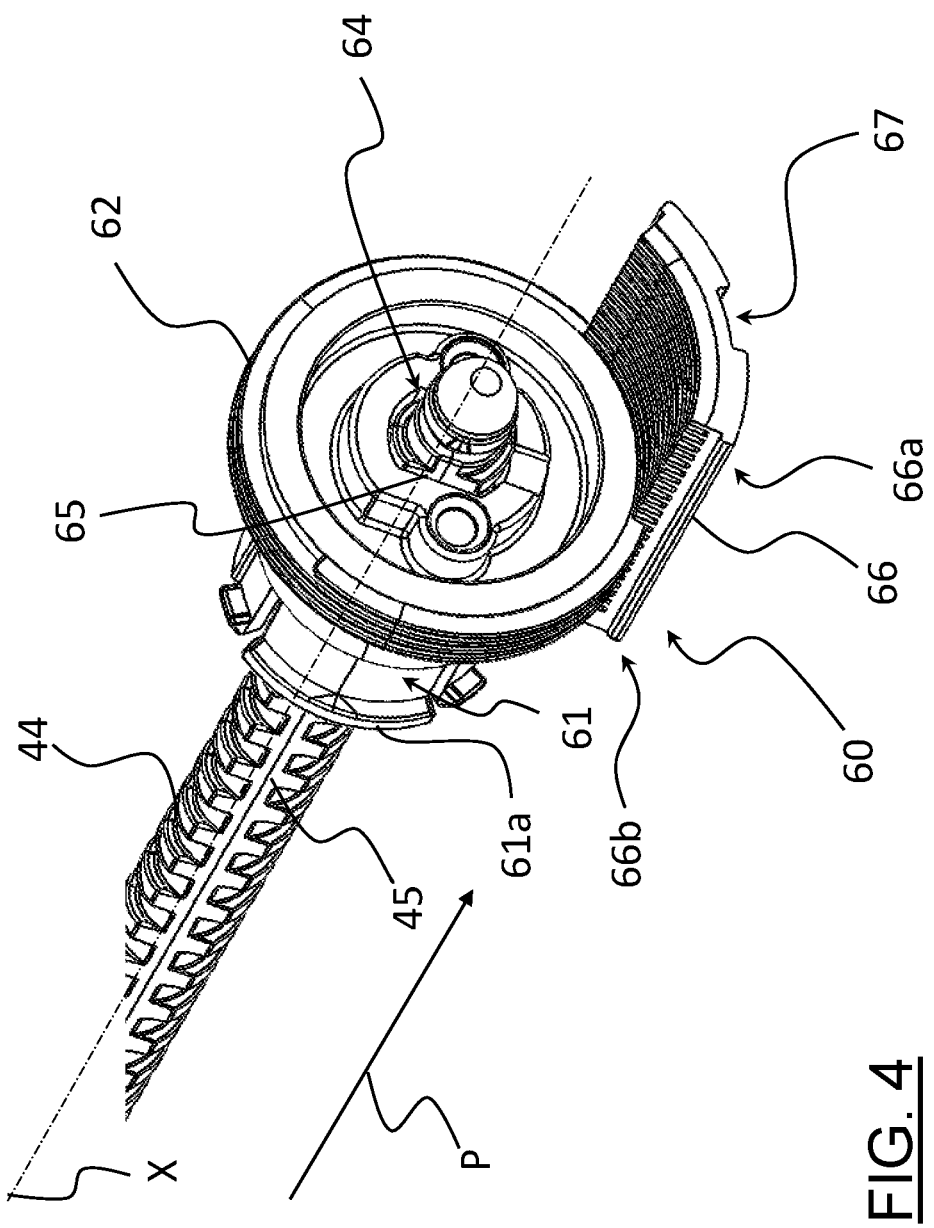
FIGS. 4 and 5 are schematic perspective views of the last dose setting device of FIG. 4 in two different setting configurations thereof subsequent to the one shown in FIG. 4.

Once such a new dose setting operation is concluded, the rack 66 is at a new axial position closer to the cartridge 17 than the previously second axial position. An example of the new axial position reached by the rack 66 is shown in FIG. 4.

The user can continue to perform the abovementioned dose setting operation and dose delivery operation till the whole drug volume initially contained in the cartridge 17 is delivered.

After one or more previous dose setting and delivery operations, when the new dose setting operation (herein referred to as last dose setting operation) is such that the dose to be set is the same or almost the same as the drug volume remaining in the cartridge 17, the rack 66 reaches an axial position such that the pinion 62 is positioned at the second free end 66b of the rack 66 opposite to the first free end 66a. An example of such an axial position is shown in FIGS. 5 and 6.

Thus, from the first dose setting and delivery operation to the last dose setting and delivery operation the rack 66 travels a total axial length towards the cartridge 17 which depends on the whole drug volume initially provided within the cartridge 17.

The user can set (and subsequently deliver) any desired dose till the rotational end stop element 70 of the pinion 62 and the rotational end stop element 80 of the rack 66 abut to each other. Such a situation is very close to the one shown in FIG. 6. In particular, it is reached upon a further small rotation of the pinion 62, and a consequent short axial movement of the rack 66, with respect to the situation shown in FIG. 6.

Should the user try to set a dose greater than the one currently and actually available drug volume in the cartridge 17, the rotational end stop element 70 of the pinion 62 abuts against the rotational end stop element 80 of the rack 66, thus preventing further relative movement between pinion 62 and rack 66 and therefore preventing the user to set such a dose.

Accordingly, the user can set as the last dose a dose which is equal to the currently and actually available drug volume in the cartridge 17.

Of course, those skilled in the art can bring numerous modifications and changes to the invention described above in order to satisfy specific and contingent requirements, all of which are within the scope of protection defined by the following claims.

The invention claimed is:

1. A drug injection device comprising:
a cartridge housing extending along a longitudinal axis and configured to house a cartridge including a predetermined drug volume;
a dose setting mechanism configured to set a drug dose to be delivered out of the cartridge;
a dose delivery mechanism configured to deliver the drug dose set by the dose setting mechanism;

wherein the dose setting mechanism comprises:
a dose setting service element configured to rotate about said longitudinal axis during the drug dose setting;
a last dose setting device configured to prevent a user to set a drug dose greater than the drug volume remaining in the cartridge after at least one previous drug dose delivery, wherein the last dose setting device comprises:
a pinion arranged coaxially to said longitudinal axis at a fixed axial position with respect to the cartridge housing and configured to rotate about the longitudinal axis together with the dose setting service element during the drug dose setting;
a rack engaged with the pinion and movable along a longitudinal direction parallel to the longitudinal axis when the pinion rotates;
wherein the pinion and the rack have mutual abutment elements configured to abut with each other and prevent further rotation of the pinion after the rack has travelled an axial length correlated to the predetermined drug volume.

2. The drug injection device according to claim 1, wherein during the drug dose setting the dose setting service element does not move along said longitudinal direction.

3. The drug injection device according to claim 1, wherein the dose setting service element is configured to move along said longitudinal direction toward the cartridge housing during the drug dose delivery.

4. The drug injection device according to claim 3, wherein during the drug dose delivery the dose setting service element does not rotate about said longitudinal axis.

5. The drug injection device according to claim 3, wherein the rack has a predetermined axial dimension which is correlated to an axial length travelled by the dose setting service element for delivering the predetermined drug volume.

6. The drug injection device according to claim 1, wherein before setting a first drug dose the pinion is located at a first free end of the rack closer to the cartridge housing and after having set the last drug dose the pinion is located at a second free end of the rack opposite to the first free end of the rack.

7. The drug injection device according to claim 1, wherein said mutual abutment elements comprise a first rotational end stop element associated with the pinion and a second rotational end stop element associated with the rack.

8. The drug injection device according to claim 7, wherein before setting a first drug dose the pinion is located at a first free end of the rack closer to the cartridge housing and after having set the last drug dose the pinion is located at a second free end of the rack opposite to the first free end of the rack, wherein the first rotational end stop element is associated with a face of the pinion located on the opposite side with respect to the cartridge housing and the second rotational end stop element is arranged at the second free end of the rack.

9. The drug injection device according to claim 1, wherein the rack is slidingly coupled to an outer case of the drug injection device.

10. The drug injection device according to claim 9, wherein the rack comprises an axial guide groove slidably coupled to an axial guide rail provided on an internal surface of the outer case of the drug injection device.

11. The drug injection device according to claim 9, wherein the pinion is arranged between the rack and at least one rib formed on an internal surface of the outer case on the opposite side with respect to the rack.

12. The drug injection device according to claim 1, wherein the dose setting service element has at least one planar surface and the pinion has at least one planar profile portion coupled to the at least one planar surface of the dose setting service element.

13. The drug injection device according to claim 1, wherein the dose setting service element is a piston rod extending along said longitudinal axis.

14. The drug injection device according to claim 13, wherein the dose setting service element has at least one planar surface and the pinion has at least one planar profile portion coupled to the at least one planar surface of the dose setting service element, wherein the pinion has a central hole coupled with the piston rod and said at least one planar profile portion is defined by a surface portion of said central hole.

* * * * *